(12) United States Patent
Jimenez et al.

(10) Patent No.: US 9,173,477 B2
(45) Date of Patent: Nov. 3, 2015

(54) ORAL CARE SYSTEM, KIT AND METHOD

(75) Inventors: Eduardo Jimenez, Manalapan, NJ (US); Alan Sorrentino, Cranbury, NJ (US); Robert Moskovich, East Brunswick, NJ (US)

(73) Assignee: COLGATE-PALMOLIVE COMPANY, New York, NY (US)

( * ) Notice: Subject to any disclaimer, the term of this patent is extended or adjusted under 35 U.S.C. 154(b) by 1023 days.

(21) Appl. No.: 13/254,449

(22) PCT Filed: Dec. 16, 2010

(86) PCT No.: PCT/US2010/060881
§ 371 (c)(1),
(2), (4) Date: Sep. 1, 2011

(87) PCT Pub. No.: WO2011/079030
PCT Pub. Date: Jun. 30, 2011

(65) Prior Publication Data
US 2012/0163902 A1   Jun. 28, 2012

Related U.S. Application Data

(63) Continuation-in-part of application No. PCT/US2009/069408, filed on Dec. 23, 2009, and a continuation-in-part of application No. PCT/US2009/069402, filed on Dec. 23, 2009.

(Continued)

(51) Int. Cl.
*A46B 11/00* (2006.01)
*A61C 19/06* (2006.01)

(52) U.S. Cl.
CPC ......... *A46B 11/0024* (2013.01); *A46B 11/0027* (2013.01); *A46B 11/0034* (2013.01);

(Continued)

(58) Field of Classification Search
CPC .................. A46B 2200/1066; A46B 11/0065; A46B 11/0079; A46B 11/0068
USPC ........... 401/132–135, 118, 123; 222/100, 105
See application file for complete search history.

(56) References Cited

U.S. PATENT DOCUMENTS

| 64,732 A | 5/1867 | Wylie |
|---|---|---|
| 261,456 A | 7/1882 | Hoffman |

(Continued)

FOREIGN PATENT DOCUMENTS

| EP | 1506726 | 2/2005 |
|---|---|---|
| FR | 850458 | 12/1939 |

(Continued)

OTHER PUBLICATIONS

International Search Report and Written Opinion in International Application No. PCT/US10/60881 mailed May 16, 2011.

(Continued)

*Primary Examiner* — David Walczak
*Assistant Examiner* — Bradley Oliver

(57) ABSTRACT

An oral care system comprising an oral care implement, such as a toothbrush, and dispenser containing a fluid detachably coupled to the tooth-brush. The invention is an oral care system comprising: a toothbrush having a cavity; a dispenser comprising a reservoir containing a fluid; a cap detachably coupled to the dispenser; wherein when the cap is coupled to the dispenser, the cap prohibits the dispenser from being inserted into the cavity; and wherein when the cap is detached from the dispenser, the dispenser can be inserted into the cavity and detachably coupled to the toothbrush.

20 Claims, 10 Drawing Sheets

Related U.S. Application Data

(60) Provisional application No. 61/410,514, filed on Nov. 5, 2010, provisional application No. 61/423,397, filed on Dec. 15, 2010, provisional application No. 61/423,414, filed on Dec. 15, 2010, provisional application No. 61/423,435, filed on Dec. 15, 2010, provisional application No. 61/423,449, filed on Dec. 15, 2010.

(52) U.S. Cl.
CPC ........... *A46B11/0065* (2013.01); *A61C 19/066* (2013.01); *A46B 2200/1066* (2013.01); *Y10T 29/49826* (2015.01)

(56) References Cited

U.S. PATENT DOCUMENTS

| | | | |
|---|---|---|---|
| 1,244,324 A | 10/1917 | Hackley | |
| 1,292,416 A | 1/1919 | Auld | |
| 1,546,516 A | 7/1925 | Smith | |
| 1,555,064 A | 9/1925 | La Mothe | |
| 1,668,511 A | 5/1928 | McLaughlin | |
| 1,701,030 A | 2/1929 | Collins | |
| 1,746,474 A | 2/1930 | Hogner | |
| 1,913,528 A | 6/1933 | White | |
| 1,975,723 A | 10/1934 | Johnssen | |
| 2,078,149 A * | 4/1937 | Lutz | 222/105 |
| D134,723 S | 1/1943 | Riksheim | |
| 2,356,874 A | 8/1944 | Nageotte | |
| 2,437,769 A | 3/1948 | Traylor | |
| 2,445,571 A | 7/1948 | Fuston | |
| 2,448,033 A | 8/1948 | Kruck | |
| 2,450,002 A * | 9/1948 | Jackson | 401/124 |
| 2,521,882 A | 9/1950 | Swift et al. | |
| 2,541,949 A | 2/1951 | Thacker et al. | |
| 2,579,899 A | 12/1951 | Burrows | |
| 2,637,060 A | 5/1953 | Cowan | |
| 2,670,881 A | 3/1954 | Sjoblom | |
| 2,676,568 A | 4/1954 | Maczynski | |
| 2,718,299 A | 9/1955 | Atwater et al. | |
| 2,771,858 A | 11/1956 | Cribbs et al. | |
| 2,800,899 A | 7/1957 | Barron | |
| 2,885,110 A | 5/1959 | Tregilgas | |
| 2,885,116 A | 5/1959 | Tregilgas | |
| 3,108,687 A | 10/1963 | Dayton | |
| 3,148,684 A | 9/1964 | Keeler | |
| 3,181,539 A | 5/1965 | Aston | |
| 3,187,758 A | 6/1965 | Eklund | |
| 3,215,320 A | 11/1965 | Heisler et al. | |
| 3,293,749 A | 12/1966 | George et al. | |
| 3,296,642 A | 1/1967 | Aylott | |
| 3,358,699 A | 12/1967 | Bau | |
| 3,359,991 A | 12/1967 | Spatz | |
| 3,359,992 A | 12/1967 | Cishek et al. | |
| 3,378,176 A | 4/1968 | Snyder | |
| 3,406,694 A | 10/1968 | Odence | |
| 3,468,612 A | 9/1969 | Aston | |
| 3,842,850 A * | 10/1974 | Sanders | 401/123 |
| 3,986,645 A | 10/1976 | Baldwin et al. | |
| 4,275,750 A * | 6/1981 | Clark | 401/123 |
| 4,296,518 A | 10/1981 | Furrier et al. | |
| 4,323,157 A | 4/1982 | Idec | |
| 4,331,267 A | 5/1982 | Duncan et al. | |
| 4,340,367 A | 7/1982 | Vadas et al. | |
| 4,350,712 A | 9/1982 | Kocharian et al. | |
| 4,384,645 A | 5/1983 | Manfredi | |
| 4,413,760 A | 11/1983 | Paton | |
| 4,506,810 A | 3/1985 | Goncalves | |
| 4,527,574 A * | 7/1985 | Manfredi | 401/124 |
| 4,641,766 A | 2/1987 | Vlasich | |
| 4,655,372 A | 4/1987 | Ross et al. | |
| 4,659,327 A | 4/1987 | Bennett et al. | |
| 4,763,815 A | 8/1988 | Von Schuckmann et al. | |
| 4,767,032 A | 8/1988 | Smith | |
| 4,776,717 A | 10/1988 | Iizuka et al. | |
| 4,808,022 A | 2/1989 | Iizuka et al. | |
| 4,826,341 A * | 5/1989 | Kwak | 401/280 |
| 4,874,117 A | 10/1989 | Kay et al. | |
| 4,879,781 A | 11/1989 | Desimone | |
| 4,886,186 A | 12/1989 | Andris | |
| 4,892,427 A | 1/1990 | Ford | |
| D310,308 S | 9/1990 | Wolsey | |
| 4,954,000 A | 9/1990 | Gueret | |
| 4,997,299 A | 3/1991 | Ohba | |
| 5,000,356 A | 3/1991 | Johnson et al. | |
| 5,011,317 A | 4/1991 | Gueret | |
| 5,016,782 A | 5/1991 | Pfanstiel | |
| 5,018,892 A | 5/1991 | Krueckel et al. | |
| 5,066,155 A | 11/1991 | English et al. | |
| 5,156,479 A | 10/1992 | Iizuka | |
| 5,199,807 A | 4/1993 | Uchida | |
| 5,234,136 A | 8/1993 | Kopis | |
| 5,294,205 A | 3/1994 | Moeck et al. | |
| 5,336,005 A | 8/1994 | Moeck et al. | |
| 5,423,623 A | 6/1995 | Bakic | |
| 5,540,361 A | 7/1996 | Fattori | |
| 5,547,302 A | 8/1996 | Dornbusch et al. | |
| 5,560,518 A | 10/1996 | Catterall et al. | |
| 5,573,341 A | 11/1996 | Iaia | |
| 5,697,531 A | 12/1997 | Fattori | |
| 5,725,133 A | 3/1998 | Iaia | |
| 5,765,573 A | 6/1998 | Gueret | |
| 5,772,347 A | 6/1998 | Gueret | |
| 5,803,640 A | 9/1998 | Nakajima et al. | |
| 5,827,002 A | 10/1998 | Nakajima | |
| 5,839,622 A | 11/1998 | Bicknell et al. | |
| 5,851,079 A | 12/1998 | Horstman et al. | |
| 5,860,572 A | 1/1999 | Harrold et al. | |
| 5,879,095 A | 3/1999 | Gueret | |
| 5,941,254 A | 8/1999 | Heler | |
| 5,996,850 A | 12/1999 | Morali et al. | |
| 6,015,293 A | 1/2000 | Rimkus | |
| 6,071,026 A | 6/2000 | Martinez et al. | |
| 6,082,918 A | 7/2000 | Gueret | |
| 6,086,276 A | 7/2000 | Gueret | |
| 6,200,055 B1 | 3/2001 | Fusaro, Jr. | |
| 6,202,247 B1 | 3/2001 | Lorenz, Jr. | |
| 6,210,061 B1 | 4/2001 | Johnson | |
| 6,213,662 B1 | 4/2001 | Aljanedi | |
| 6,220,773 B1 | 4/2001 | Wiegner et al. | |
| 6,224,573 B1 | 5/2001 | Yeager et al. | |
| 6,227,209 B1 | 5/2001 | Kim et al. | |
| 6,238,117 B1 | 5/2001 | Griebel et al. | |
| 6,290,417 B1 | 9/2001 | Kaminski | |
| 6,325,076 B1 * | 12/2001 | Ramirez | 132/309 |
| 6,368,001 B1 | 4/2002 | Roeder | |
| 6,398,439 B1 | 6/2002 | Szekely | |
| 6,406,694 B1 | 6/2002 | LaRosa | |
| 6,450,716 B1 | 9/2002 | Szekely | |
| 6,672,783 B1 | 1/2004 | Licata et al. | |
| 6,688,317 B2 | 2/2004 | Gueret | |
| 6,688,793 B2 | 2/2004 | Goyet | |
| 6,688,796 B1 | 2/2004 | Liu | |
| 6,745,781 B2 | 6/2004 | Gueret | |
| 6,746,170 B2 | 6/2004 | Delage | |
| 6,752,558 B1 | 6/2004 | Hsu | |
| 6,824,018 B1 | 11/2004 | Eaddy et al. | |
| 6,866,438 B2 | 3/2005 | Bauer et al. | |
| 6,874,665 B2 | 4/2005 | Doherty et al. | |
| 6,880,999 B2 | 4/2005 | Biegel et al. | |
| 6,918,511 B1 | 7/2005 | Spatz et al. | |
| 6,923,587 B2 | 8/2005 | Lee | |
| 6,957,753 B2 | 10/2005 | Tani | |
| 7,044,671 B2 | 5/2006 | Parikh et al. | |
| 7,051,642 B2 | 5/2006 | Kageyama | |
| 7,055,527 B2 | 6/2006 | Tien | |
| 7,086,564 B1 | 8/2006 | Corrigan | |
| 7,086,796 B2 | 8/2006 | Severa | |
| 7,089,564 B2 | 8/2006 | Chen et al. | |
| 7,114,505 B2 | 10/2006 | Bauer et al. | |
| 7,143,462 B2 | 12/2006 | Hohlbein | |
| 7,144,175 B2 | 12/2006 | Biegel | |
| 7,168,435 B2 | 1/2007 | Vieu et al. | |
| 7,192,212 B2 | 3/2007 | Gutberlet et al. | |
| 7,217,054 B2 | 5/2007 | Noguchi | |
| 7,226,231 B2 | 6/2007 | Py et al. | |

(56) References Cited

U.S. PATENT DOCUMENTS

| | | | |
|---|---|---|---|
| 7,237,974 B2 * | 7/2007 | Pfenniger et al. | 401/123 |
| 7,237,975 B2 | 7/2007 | Noguchi | |
| 7,303,348 B2 | 12/2007 | Phipps et al. | |
| 7,309,184 B2 | 12/2007 | Butcher et al. | |
| 7,347,360 B2 | 3/2008 | Lasch et al. | |
| 7,374,360 B1 | 5/2008 | Szekely | |
| 7,396,180 B2 | 7/2008 | Bugla et al. | |
| 7,401,373 B2 | 7/2008 | Tybinkowski et al. | |
| 7,461,988 B2 | 12/2008 | Albisetti | |
| 7,465,113 B2 | 12/2008 | Gueret | |
| 7,474,048 B2 | 1/2009 | Forrest et al. | |
| 7,520,406 B2 | 4/2009 | Jaichandra et al. | |
| 7,557,936 B2 | 7/2009 | Dickinson | |
| 7,641,411 B2 | 1/2010 | Biegel | |
| 7,651,291 B2 | 1/2010 | Py et al. | |
| 7,665,923 B2 | 2/2010 | Py et al. | |
| 8,511,323 B2 * | 8/2013 | Jimenez et al. | 401/175 |
| 8,636,433 B2 * | 1/2014 | Lerner et al. | 401/123 |
| 8,757,912 B2 * | 6/2014 | Jimenez et al. | 401/123 |
| 2002/0054783 A1 | 5/2002 | Gueret | |
| 2002/0073496 A1 | 6/2002 | Kim | |
| 2002/0090250 A1 * | 7/2002 | Blecher | 401/175 |
| 2003/0057236 A1 | 3/2003 | Delage | |
| 2004/0028456 A1 | 2/2004 | Giraldo | |
| 2005/0006409 A1 | 1/2005 | Ganzeboom | |
| 2005/0026774 A1 | 2/2005 | Nolan | |
| 2005/0036821 A1 * | 2/2005 | Pfenniger et al. | 401/123 |
| 2006/0207627 A1 | 9/2006 | Thorpe et al. | |
| 2006/0233588 A1 | 10/2006 | Gueret | |
| 2006/0269354 A1 | 11/2006 | Lane | |
| 2006/0275225 A1 | 12/2006 | Prencipe et al. | |
| 2007/0007302 A1 | 1/2007 | Jaichandra et al. | |
| 2007/0079845 A1 | 4/2007 | Gueret | |
| 2007/0227553 A1 | 10/2007 | Gueret | |
| 2007/0231055 A1 | 10/2007 | Albisetti | |
| 2007/0267436 A1 | 11/2007 | Abbott et al. | |
| 2007/0292194 A1 | 12/2007 | Albisetti et al. | |
| 2008/0063464 A1 | 3/2008 | Prague | |
| 2008/0089733 A1 | 4/2008 | Lochak | |
| 2008/0189888 A1 | 8/2008 | Hohlbein | |
| 2008/0274066 A1 | 11/2008 | Montgomery | |
| 2009/0074679 A1 | 3/2009 | Silverman | |
| 2009/0261007 A1 | 10/2009 | Sanchez | |
| 2009/0317432 A1 | 12/2009 | Kergosien | |
| 2010/0067969 A1 * | 3/2010 | Kang | 401/118 |
| 2012/0034016 A1 * | 2/2012 | Jimenez et al. | 401/174 |
| 2012/0257920 A1 * | 10/2012 | Jimenez et al. | 401/118 |
| 2012/0275843 A1 * | 11/2012 | Jimenez et al. | 401/268 |

FOREIGN PATENT DOCUMENTS

| | | |
|---|---|---|
| FR | 907669 | 3/1946 |
| FR | 1596074 | 6/1970 |
| FR | 2597734 | 10/1987 |
| GB | 2085717 | 5/1982 |
| GB | 2280361 | 2/1995 |
| JP | 48-093167 | 12/1973 |
| WO | WO 2004/112637 | 12/2004 |
| WO | WO 2008/062935 | 5/2008 |
| WO | WO 2009/151455 | 12/2009 |

OTHER PUBLICATIONS

International Search Report and Written Opinion in ternational Application No. PCT/US09/069408 mailed Jul. 23, 2010.
International Search Report and Written Opinion in International Application No. PCT/US09/069402 mailed Jul. 23, 2010.
International Search Report and Written Opinion in International Application No. PCT/US10/060861 mailed Jun. 8, 2011.
International Search Report and Written Opinion in International Application No. PCT/US10/049102 mailed Jun. 7, 2011.

* cited by examiner

ORAL CARE SYSTEM, KIT AND METHOD

CROSS-REFERENCE TO RELATED APPLICATIONS

This application is a national stage entry under 35 U.S.C. §371 of International Patent Application No. PCT/US2010/060881, filed 16 Dec. 2010, which is a continuation in part of International Application No. PCT/US2009/069408 filed on Dec. 23, 2009 and International Application No. PCT/US2009/069402 filed on Dec. 23, 2009 PCT/US2010/060881 also claims priority to U.S. Provisional Application No. 61/410,514 filed on Nov. 5, 2010; U.S. Provisional Application No. 61/423,397 filed on Dec. 15, 2010; U.S. Provisional Application No. 61/423,414 filed on Dec. 15, 2010; U.S. Provisional Application No. 61/423,435 filed on Dec. 15, 2010; and U.S. Provisional Application No. 61/423,449 filed on Dec. 15, 2010, all of which are incorporated herein by reference.

FIELD OF THE INVENTION

The present invention relates generally to oral care systems, kits and methods, and more specifically to a system, kit and method including a toothbrush and a dispenser containing a fluid that detachably couples to the toothbrush.

BACKGROUND OF THE INVENTION

Oral care products or agents are applied in different ways. For example, without limitation, a common technique used for applying tooth whitening products is to cast an impression of a person's teeth and provide a tray of the shape of this impression. A person then only needs to add a whitening composition to the tray and to apply the tray to his/her teeth. The tray is left in place for a period of time and then removed. After a few treatments the teeth gradually whiten. Another technique is to use a strip that has a whitening composition on one surface. This strip is applied to a person's teeth and left in place for about 30 minutes. After several applications the teeth are gradually whitened. Yet another technique is to apply a whitening composition to teeth using a small brush. This brush is repeatedly dipped back into the container during the application of the tooth whitening composition to one's teeth. After a few treatments the teeth gradually whiten.

A problem with existing brushing techniques is that saliva in the mouth contains the enzyme catalase. This enzyme will catalyze the decomposition of peroxides. The brush can pick up some catalase during the application of some of the whitening product to teeth and transport that catalase back to the bottle. This catalase now in the bottle can degrade the peroxide in the bottle. Another problem with this latter technique is that it does not adapt for use with anhydrous whitening compositions. Here the brush may transport moisture from saliva from the mouth back into the bottle. This will have a negative effect on the whitening composition by potentially decomposing the peroxide active ingredient. In addition, if a person washes the brush each time after use, moisture from the wet bristles can enter the bottle.

While tray-based systems are suitable, many people do not use them due to the fact that they tend to be uncomfortable and/or awkward. Moreover, in order to use a whitening tray, a user must keep the tray and the required components at hand. This not only requires extra storage space in already cramped bathroom cabinets but also requires that the user remember to use the whitening system. Furthermore, these tray-based systems are not conveniently portable for transport and/or travel.

In addition to difficulties in applying some oral care products, storage is sometimes cumbersome and inconvenient for the user. The oral care product must typically be stored separately from oral care tooth cleaning implements such as a toothbrush since the oral care product package and toothbrush heretofore are generally treated as separate and distinct parts of an oral care regimen.

A more portable, compact and convenient way to store oral care products, and to dispense and apply those oral care products to oral surfaces is desired.

BRIEF SUMMARY OF THE INVENTION

Embodiments of the present invention provide an efficient, compact, and portable oral care system that combines an oral care implement, such as a toothbrush, with a fluid dispenser. Advantageously, certain embodiments are especially suited for easy transport and/or travel.

Exemplary embodiments of the present invention are directed to a toothbrush that detachably retains a removable dispenser containing a fluid reservoir. In some exemplary embodiments, the oral care system includes fluids, either active or non-active agents, that may include without limitation, whitening, enamel protection, anti-sensitivity, fluoride, tartar protection, or other fluidic materials. The dispenser can be detachably coupled to the toothbrush. In one embodiment, the dispenser may be at least partially located within the handle of the toothbrush so that a portion of the dispenser protrudes from the toothbrush. The dispenser can be completely removable from the toothbrush in certain embodiments so that the user can apply the fluid to his/her oral surfaces with ease, and then re-couple the dispenser to the toothbrush for convenient storage. In certain embodiments, the dispenser may be a pen-like component.

In one embodiment, the invention can be an oral care system comprising: a toothbrush having a cavity and a plug in the cavity; a dispenser comprising a reservoir containing a fluid and a dispensing orifice; a cap detachably coupled to the dispenser that seals the dispensing orifice; wherein when the cap is coupled to the dispenser, the cap prohibits the dispenser from being inserted into the cavity; and wherein when the cap is detached from the dispenser, the dispenser can be inserted into the cavity so that the plug penetrates the dispensing orifice and the dispenser is detachably coupled to the toothbrush.

In another embodiment, the invention can be an oral care system comprising: a toothbrush having a cavity extending along a longitudinal axis and an opening forming a passageway into the cavity, the opening having a first transverse cross-sectional profile; a dispenser comprising a housing having a reservoir containing a fluid and a dispensing orifice, the housing having a second transverse cross-sectional profile that fits entirely within the first transverse cross-sectional profile; and a cap detachably coupled to the dispenser, the cap having a portion having a third cross-sectional profile that does not fit entirely within the first transverse cross-sectional profile.

In yet another embodiment, the invention can be an oral care system comprising: a toothbrush having a cavity; a dispenser comprising a reservoir containing a fluid; a cap detachably coupled to the dispenser; wherein when the cap is coupled to the dispenser, the cap prohibits the dispenser from being inserted into the cavity; and wherein when the cap is detached from the dispenser, the dispenser can be inserted into the cavity and detachably coupled to the toothbrush.

In still another embodiment, the invention can be an oral care system comprising: a toothbrush having a cavity; a dispenser comprising a reservoir containing a fluid; the dispenser alterable between: (1) a storage state in which the dispenser is located within the cavity and detachably coupled to the toothbrush; and (2) an application state in which the dispenser is separated from the toothbrush; a cap detachably coupled to the dispenser that seals the dispensing orifice; wherein when the cap is coupled to the dispenser, the dispenser can not altered into the storage state; and wherein when the cap is detached from the dispenser, the dispenser can be altered into the storage state.

In certain exemplary embodiments, any suitable fluid may be used with embodiments and methods described herein according to the present invention. Accordingly, the oral care treatment system may be any type of system including without limitation tooth whitening, enamel protection, anti-sensitivity, fluoride, tartar protection/control, and others. The invention is expressly not limited to any particular type of oral care system or oral care material, unless specifically claimed.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The features of the exemplified embodiments will be described with reference to the following drawings in which like elements are labeled similarly. The present invention will become more fully understood from the detailed description and the accompanying drawings, wherein.

DETAILED DESCRIPTION OF THE INVENTION

Figure 1:
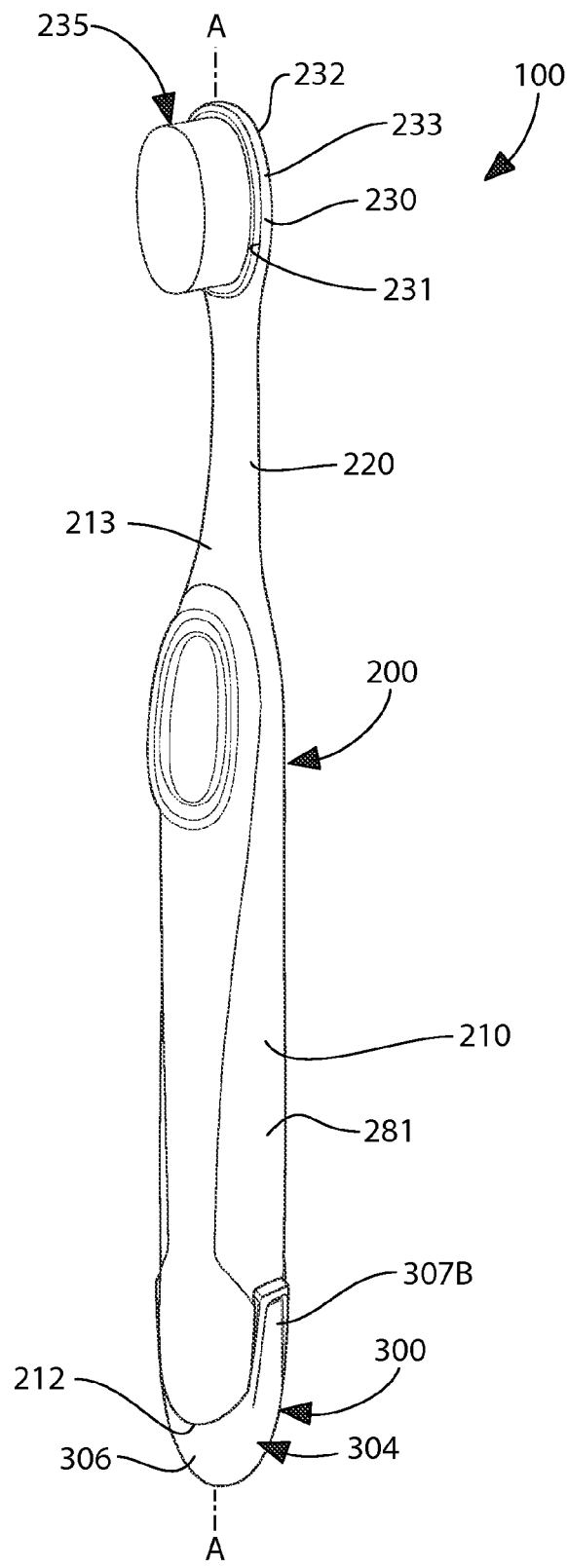
FIG. 1 is a front perspective view of an oral care system including a toothbrush and a fluid dispenser according to one embodiment of the present invention, wherein the dispenser is detachably coupled to the toothbrush in the storage state.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

Exemplary embodiments of the present invention will now be described with respect to one possible oral care system. Embodiments of the oral care system may include without limitation the following fluids: tooth whitening, antibacterial, enamel protection, anti-sensitivity, anti-inflammatory, anti-attachment, fluoride, tartar control/protection, flavorant, sensate, colorant and others. However, other embodiments of the present invention may be used to store and dispense any suitable type of fluid and the invention is expressly not limited to any particular oral care system or oral care material alone.

Figure 2:
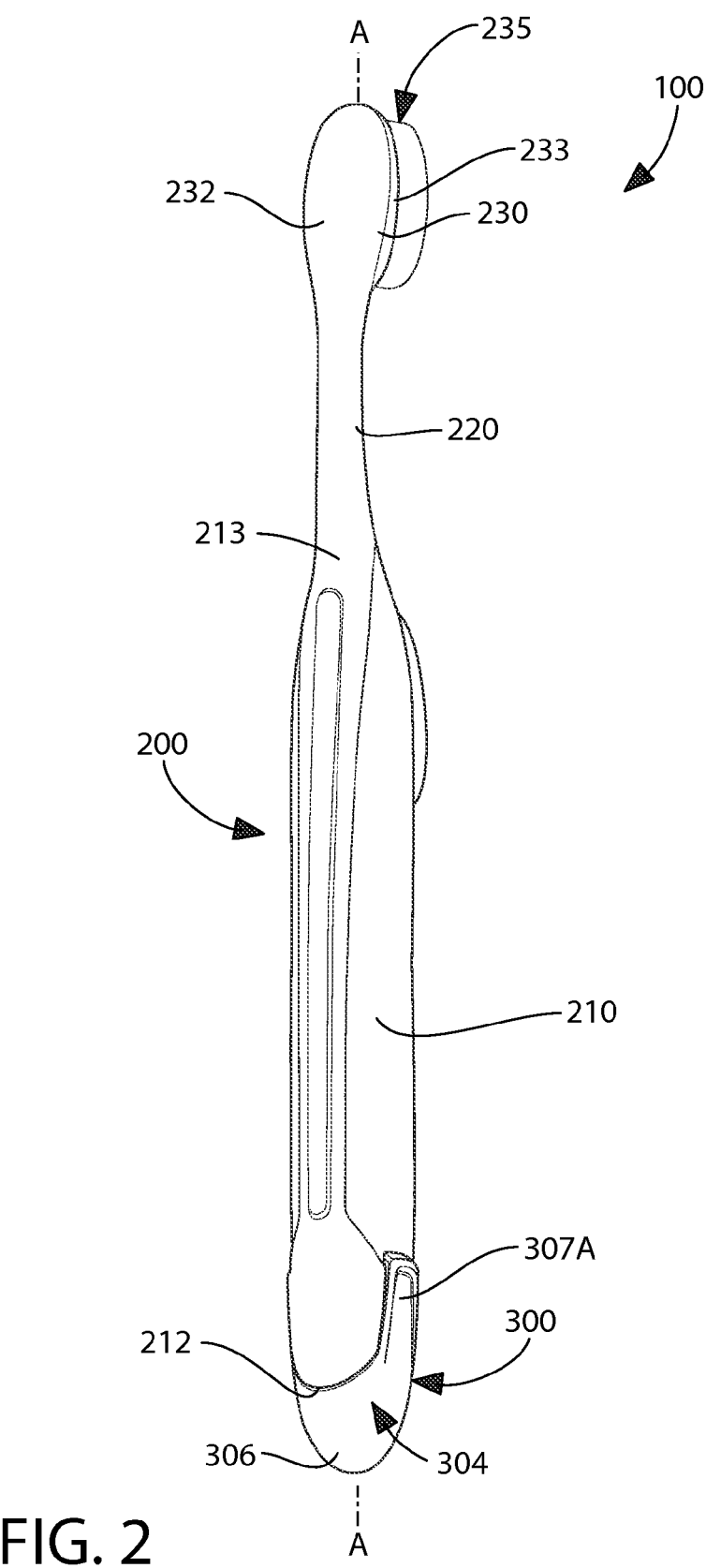
FIG. 2 is a rear perspective view of the oral care system of FIG. 1.

Referring to FIGS. 1-2, an oral care system 100 is illustrated according to one embodiment of the present invention. The oral care system 100 is a compact readily portable self-contained user-friendly system that comprises all of the necessary components and chemistries necessary for a user to perform a desired oral care treatment routine. As will be described in greater detail below, the oral care system 100 in one exemplary embodiment comprises a modified toothbrush 200 having a removable dispenser 300 disposed at least partially within its handle 210. Because the dispenser 300 is located within the handle 210 of the toothbrush 200, the oral care system 100 is portable for travel, easy to use, and reduces the amount of required storage space. Furthermore, since the toothbrush 200 and dispenser 300 are housed together, the user is less likely to misplace the dispenser 300 and more inclined to maintain the oral treatment routine with the dispenser 300 since brushing will remind the user to simply detach and apply the contents of the dispenser 300.

As discussed above, the oral care system 100 generally comprises the toothbrush 200 and the dispenser 300. While the invention is described herein with respect to the use of a toothbrush as one of the two primary components of the oral care system 100, it is to be understood that other alternate oral care implements can be used within the scope of the invention, including tongue cleaners, tooth polishers and specially designed ansate implements having tooth engaging elements. In certain instances, the toothbrush 200 may include tooth engaging elements that are specifically designed to increase the effect of the oral care material in the dispenser on the teeth. For example, the tooth engaging elements may include elastomeric wiping elements that assist in removing stains from teeth and/or assist with forcing the oral care material into the tubules of the teeth. Moreover, while the toothbrush 200 is exemplified as a manual toothbrush, the toothbrush may be a powered toothbrush in certain embodiments of the invention. It is to be understood that the inventive system can be utilized for a variety of intended oral care needs by filling the dispenser 300 with any fluid, such as an oral care agent that achieves a desired oral effect. In one embodiment, the fluid is free of (i.e., is not) toothpaste as the dispenser 300 is intended to augment not supplant the brushing regimen. The fluid can be selected to complement a toothpaste formula, such as by coordinating flavors, colors, aesthetics, or active ingredients.

The toothbrush 200 generally comprises a handle 210, a neck 220 and a head 230. The handle 210 provides the user with a mechanism by which he/she can readily grip and manipulate the toothbrush 200. The handle 210 may be formed of many different shapes, sizes and materials and may be formed by a variety of manufacturing methods that are well-known to those skilled in the art. Preferably, the handle 210 can house the dispenser 300 therein as described in detail below. If desired, the handle 210 may include a suitable textured grip made of soft elastomeric material. The handle 210 can be a single or multi-part construction. The handle 210 extends from a proximal end 212 to a distal end 213 along a longitudinal axis A-A. A cavity 280 (FIG. 4) is formed within the handle 210. An opening 215 is provided at the proximal end 212 of the handle 210 that provides a passageway into the cavity through which the dispenser 300 can be inserted and retracted. While the opening 215 is located at the proximal end 212 of the handle 210 in the exemplified embodiment, the opening 215 may be located at other positions on the handle 210 in other embodiments of the invention. For example, the opening 215 may be located on a longitudinal surface of the handle 210 (e.g., the front surface, the rear surface and/or the side surfaces) and be elongated to provide sufficient access to the cavity 280.

The handle 210 transitions into the neck 220 at the distal end 213. While the neck 220 generally has a smaller transverse cross-sectional area than the handle 220, the invention is not so limited. Broadly speaking, the neck 220 is merely the transition region between the handle 210 and the head 230 and can conceptually be considered as a portion of the handle 210. In this manner, the head 230 is connected to the distal end 213 of the handle 210 (via the neck 220).

The head 230 and the handle 210 of the toothbrush 200 are formed as a single unitary structure using a molding, milling, machining or other suitable process. However, in other embodiments, the handle 210 and the head 230 may be formed as separate components which are operably connected at a later stage of the manufacturing process by any suitable technique known in the art, including without limitation thermal or ultrasonic welding, a tight-fit assembly, a coupling sleeve, threaded engagement, adhesion, or fasteners. Whether the head 230 and the handle 210 are of a unitary or multi-piece construction (including connection techniques) is not limiting of the present invention, unless specifically claimed. In some embodiments of the invention, the head 230 may be detachable (and replaceable) from the handle 210 using techniques known in the art.

The head 230 generally comprises a front surface 231, a rear surface 232 and a peripheral side surface 233 that extends between the front and rear surfaces 231, 232. The front surface 231 and the rear surface 232 of the head 230 can take on a wide variety of shapes and contours, none of which are limiting of the present invention. For example, the front and rear surfaces 231, 232 can be planar, contoured or combinations thereof. Moreover, if desired, the rear surface 232 may also comprise additional structures for oral cleaning or tooth engagement, such as a soft tissue cleaner or a tooth polishing structure. An example of a soft tissue cleaner is an elastomeric pad comprising a plurality of nubs and or ridges. An example of a tooth polishing structure can be an elastomeric element, such as a prophy cup(s) or elastomeric wipers. Furthermore, while the head 230 is normally widened relative to the neck 220 of the handle 210, it could in some constructions simply be a continuous extension or narrowing of the handle 210.

The front surface 231 of the head 230 comprises a collection of oral cleaning elements such as tooth engaging elements 235 extending therefrom for cleaning and/or polishing contact with an oral surface and/or interdental spaces. While the collection of tooth engaging elements 235 is suited for brushing teeth, the collection of tooth engaging elements 235 can also be used to polish teeth instead of or in addition to cleaning teeth. As used herein, the term "tooth engaging elements" is used in a generic sense to refer to any structure that can be used to clean, polish or wipe the teeth and/or soft oral tissue (e.g. tongue, cheek, gums, etc.) through relative surface contact. Common examples of "tooth engaging elements" include, without limitation, bristle tufts, filament bristles, fiber bristles, nylon bristles, spiral bristles, rubber bristles, elastomeric protrusions, flexible polymer protrusions, combinations thereof and/or structures containing such materials or combinations. Suitable elastomeric materials include any biocompatible resilient material suitable for uses in an oral hygiene apparatus. To provide optimum comfort as well as cleaning benefits, the elastomeric material of the tooth or soft tissue engaging elements has a hardness property in the range of A8 to A25 Shore hardness. One suitable elastomeric material is styrene-ethylene/butylene-styrene block copolymer (SEBS) manufactured by GLS Corporation. Nevertheless, SEBS material from other manufacturers or other materials within and outside the noted hardness range could be used.

The tooth engaging elements 235 of the present invention can be connected to the head 230 in any manner known in the art. For example, staples/anchors, in-mold tufting (IMT) or anchor free tufting (AFT) could be used to mount the cleaning elements/tooth engaging elements. In AFT, a plate or membrane is secured to the brush head such as by ultrasonic welding. The bristles extend through the plate or membrane. The free ends of the bristles on one side of the plate or membrane perform the cleaning function. The ends of the bristles on the other side of the plate or membrane are melted together by heat to be anchored in place. Any suitable form of cleaning elements may be used in the broad practice of this invention. Alternatively, the bristles could be mounted to tuft blocks or sections by extending through suitable openings in the tuft blocks so that the base of the bristles is mounted within or below the tuft block.

The toothbrush 200 and the dispenser 300 are non-unitary separate structures that are specially designed to be detachably coupled together when in an assembled state (referred to herein as a storage state) and completely isolated and separated from one another when in a disassembled state (referred to herein as an application state). The toothbrush 200 and the dispenser 300 are illustrated in the storage state in FIGS. 1-2 and in the application state in FIG. 3. The dispenser 300 can be slidably manipulated and altered between the storage state (FIGS. 1-2) in which the dispenser 300 is located (or docked)

in the toothbrush handle 210 and the application state (FIG. 3) in which the dispenser 300 is removed from the handle 210 by the user as desired.

Figure 4:
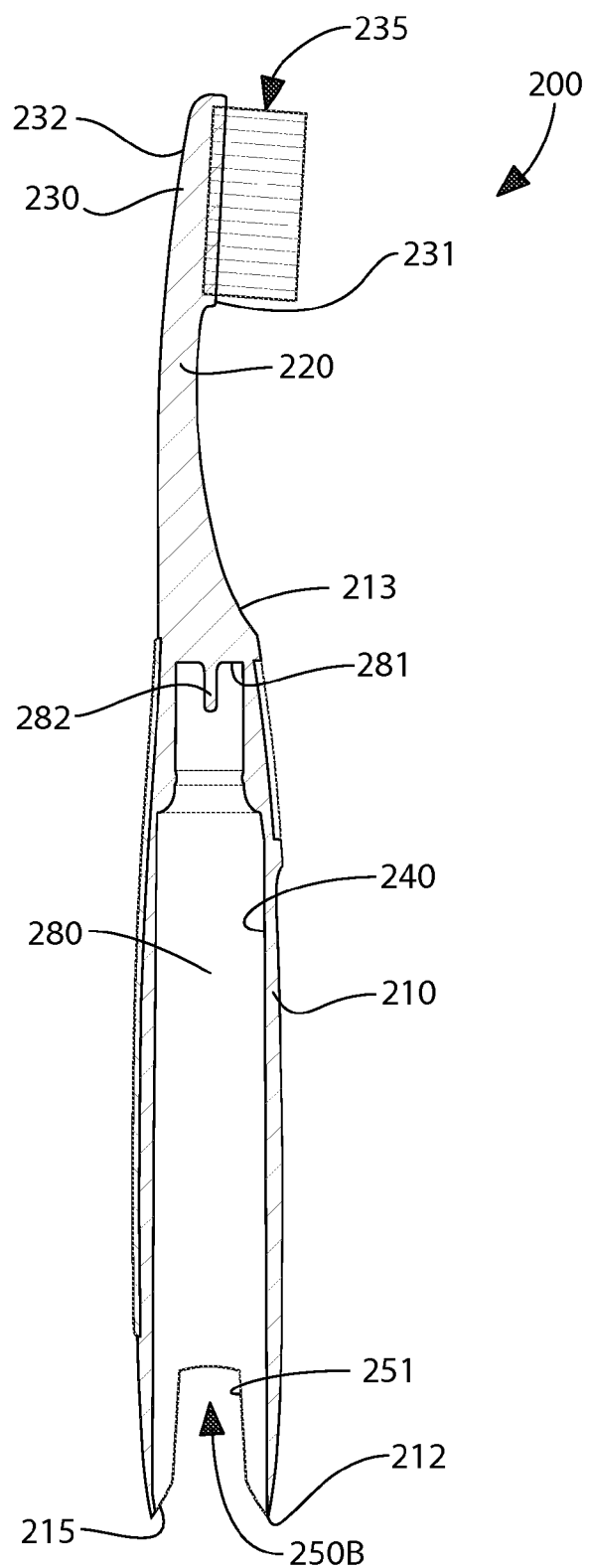
FIG. 4 is a longitudinal cross-sectional view of the toothbrush of the oral care system of FIG. 3.

Referring now to FIG. 4, additional details of the handle 210 of the toothbrush 200 will be described. As mentioned above, the toothbrush 200 comprises an internal cavity 280 in which the dispenser 300 can be inserted (i.e., slid) to effectuate a detachable coupling between the dispenser 300 and the toothbrush 200. The cavity 280 if formed by the inner surface 240 of the toothbrush 200 and extends along the longitudinal axis A-A of the toothbrush 200 from an opening 215 to a transverse end wall 281. The opening 215 forms a passageway into the cavity 280 through which the dispenser 300 can be axially translated.

A plug 282 extends axially from the transverse end wall 281. In the exemplified embodiment, the plug 282 is integrally formed with the handle 210 of the toothbrush 200. However, in other embodiments, the plug 282 may be a separate component and/or formed of a different material. As discussed in greater detail below, the plug 282 is provided as a means to seal a dispensing orifice 318 of the dispenser 300 when the dispenser 300 is in the storage state to prevent the fluid from leaking and/or drying out (see FIG. 6).

Figure 8:
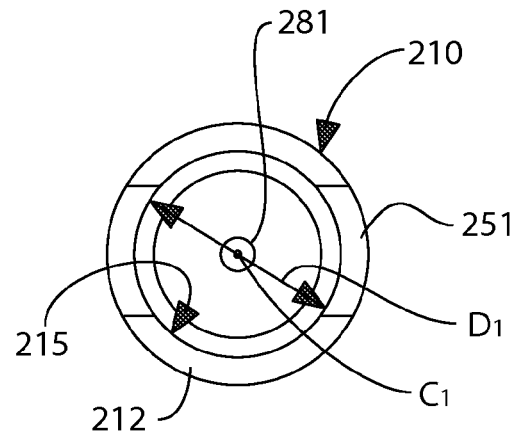
FIG. 8 is a transverse cross-sectional profile of the opening of the toothbrush of the oral care system of FIG. 3 taken along view XIII-XIII of FIG. 3.

In the exemplified embodiment, the cavity 280 has generally circular transverse-cross sectional profile. However, the invention is not so limited and in other embodiments, the cavity 280 may have non-circular transverse cross-sectional profiles as desired. As can be seen in FIG. 8, the opening 215, which is defined by the proximal edge 251 of the toothbrush 200 has a circular transverse cross-sectional profile in the exemplified embodiment. However, as with the cavity 280, the opening 215 may have non-circular transverse cross-sectional profiles as desired. The transverse cross-sectional profile of the opening 215 has a center point $C_1$ and a diameter $D_1$. As discussed below, the size and/or shape of the transverse cross-sectional profile of the opening 215 is selected to cooperate with the transverse cross-sectional profiles of the dispenser 300 and detachable cap 700 so that: (1) the dispenser 300 can be inserted into the cavity 280 when the cap 700 is detached from the dispenser 300; and (2) the dispenser 300 can not be inserted into the cavity 280 when the cap 700 is coupled to the dispenser 300. This will be described in greater detail below.

Figure 3:
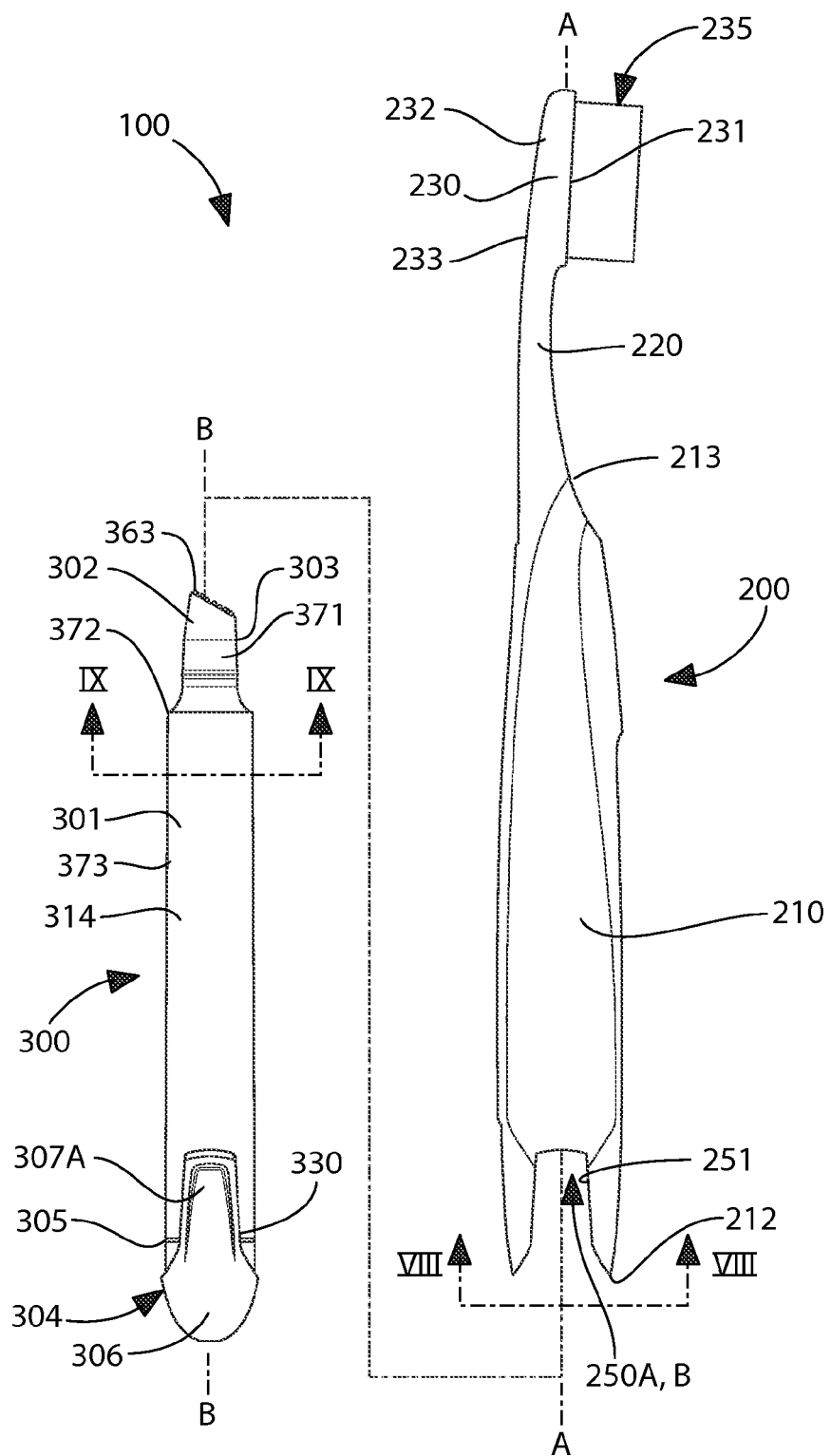
FIG. 3 is a left side view of the oral care system of FIG. 1, wherein the fluid dispenser is fully detached from the toothbrush and in an application state.
Figure 5:
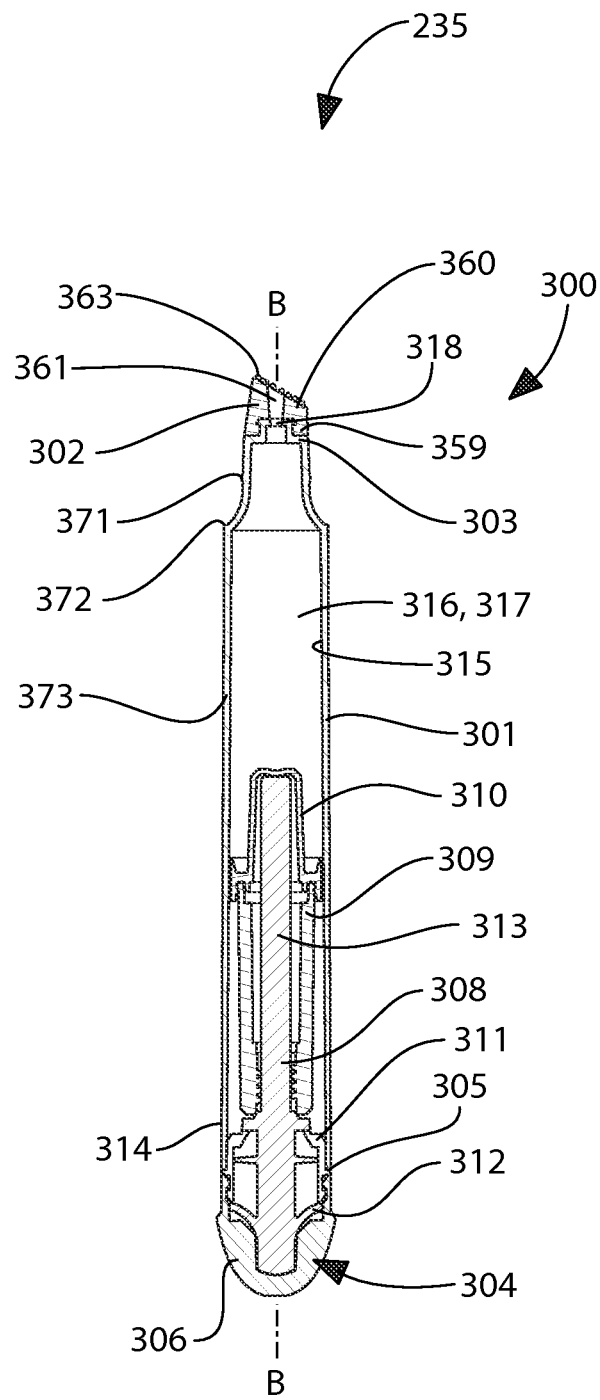
FIG. 5 is a longitudinal cross-sectional view of the fluid dispenser of the oral care system of FIG. 3.

Referring now to FIGS. 3 and 5 concurrently, an embodiment of the dispenser 300 will be described in greater detail. Generally, the dispenser 300 is an elongated tubular pen-like structure that extends along a longitudinal axis B-B. The dispenser 300 generally comprises a housing 301, an applicator 302 located at a distal end 303 of the housing 301, and a rotatable actuator 304 located at a proximal end 305 of the housing 301. The dispenser 300 is designed so as to be capable of being operated to dispense the fluid stored therein using a single hand. Specifically, the dispenser 300 is positioned in a user's hand so that the rotatable actuator 304 is lodged in the palm of the user's hand. The user then uses the fingers of that same hand to rotate the housing 301 relative to the actuator 303. As a result, the fluid contained therein is dispensed from the dispenser 300. While a rotatable actuator 304 is exemplified as the structural mechanism that is activated by the user to dispense the fluid from the dispenser's internal reservoir 317, it is to be understood that other fluid delivery mechanism can be utilized, including without limitation mechanical pumps, electrical pumps, compressible bladders, ratchets, syringe dispensers and/or combinations thereof. Unless specifically recited in a claim, the invention is not to be limited in any manner to the delivery mechanism of the dispenser 300.

The housing 301 is constructed of a material that is sufficiently rigid to provide the necessary structural integrity for the dispenser 300. For example, the housing 301 can be formed of a moldable hard plastic. Suitable hard plastics include polymers and copolymers of ethylene, propylene, butadiene, vinyl compounds and polyesters such as polyethylene terephthalate. The chosen plastic(s), however, should be compatible with the oral care material that is to be stored within the dispenser 300 and should not be corroded or degraded by the oral care agents.

While the housing 301 is exemplified as a single layer construction, in certain embodiments, the housing 301 may be a multilayer construction. In certain multi-layer embodiments, an inner layer can be formed from the hard plastic materials described immediately above while an outer layer can be formed of a soft resilient material, such as an elastomeric material. Suitable elastomeric materials include thermoplastic elastomers (TPE) or other similar materials used in oral care products. The elastomeric material of the outer layer may have a hardness durometer measurement ranging between A13 to A50 Shore hardness, although materials outside this range may be used. A suitable range of the hardness durometer rating is between A25 to A40 Shore hardness. While an over-molding construction is one suitable method of forming the outer layer, a suitable deformable thermoplastic material, such as TPE, may be formed in a thin layer and attached to inner layer with an appropriate adhesive, sonic welding, or by other means.

The housing 301 is an elongated hollow tubular structure extending along the longitudinal axis B-B from the proximal end 305 to the distal end 303. The housing 301 comprises a nozzle portion 371 to which the applicator 302 is coupled, a shoulder portion 371, and a barrel portion 372. The shoulder portion 371 is the transition between the narrow nozzle portion 371 and the larger barrel portion 373. In the exemplified embodiment, the barrel portion 373 has a substantially constant transverse cross-sectional profile extending from the shoulder portion 372 to the distal end 312 of the housing 301. However, in other embodiments, the barrel portion 373 may have a tapered transverse cross-sectional profile. Moreover, in certain embodiments, the housing 301 may not contain a nozzle portion 371 but may merely comprise a barrel portion 373 along the entire length of the housing 301.

Figure 9:
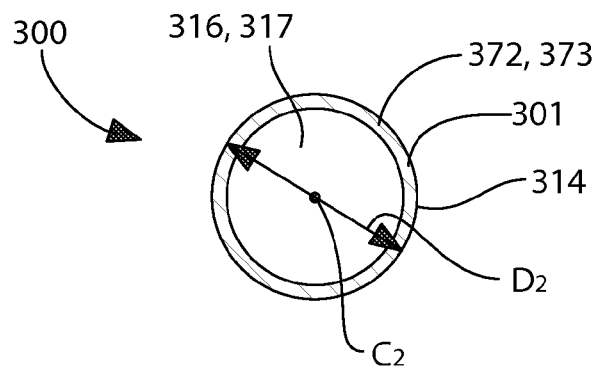
FIG. 9 is a transverse cross-sectional profile of the housing of the fluid dispenser of the oral care system of FIG. 3 taken along view IX-IX of FIG. 3.

In the exemplified embodiment, the housing 301 has a circular transverse cross-sectional profile at both the nozzle portion 371 and the barrel portion 373 (shown in FIGS. 4-5). Of course, in other embodiments, the transverse cross-sectional profile of the housing 301 can take on non-circular shapes as desired. As shown in FIG. 9, transverse cross-sectional profile of the shoulder portion 372 at its maximum size (which also corresponds to the transverse cross-sectional profile of the barrel portion 373) has a center point $C_2$ and a diameter $D_2$ (measured to an outer surface 314 of the housing 301). As discussed below, the size and/or shape of the transverse cross-sectional profile of the shoulder portion 372 of the housing 301 is selected to cooperate with the transverse cross-sectional profile of the opening 215 so that the dispenser 300 can be inserted (i.e. slid) into the cavity 280 when the cap 700 is detached from the dispenser 300. This will be described in greater detail below.

The housing 301 comprises an outer surface 314 and an inner surface 315 that forms an elongated internal cavity 316. As discussed in greater detail below, when the dispenser 300 is fully assembled, the internal cavity 316 of the housing 301 acts as a reservoir 317.

The reservoir 317 contains the desired fluid or product, which can be any active or inactive oral care agent. The oral care agent and/or its carrier may be in any form such as a solid or a flowable material including without limitation viscous pastes/gels or less viscous liquid compositions. The fluid is a flowable material having a low viscosity in certain embodiments. Any suitable fluid can be used in the present invention. For example, the fluid can be an oral care agent that includes whitening agents, including without limitation, peroxide containing tooth whitening compositions. Suitable peroxide containing tooth whitening compositions are disclosed in U.S. patent Ser. No. 11/403,372, filed Apr. 13, 2006, to the present assignee, the entirety of which is hereby incorporated by reference. While a tooth whitening agent and a sensitivity agent are two of the exemplified active agents in the present invention, any other suitable oral care agents can be used with embodiments of the present invention and, thus, stored within the reservoir 317. Contemplated fluids can be oral care agents including active or non-active ingredients, including without limitation, antibacterial agents; oxidative or whitening agents; enamel strengthening or repair agents; tooth erosion preventing agents; anti-sensitivity ingredients; gum health actives; nutritional ingredients; tartar control or anti-stain ingredients; enzymes; sensate ingredients; flavors or flavor ingredients; breath freshening ingredients; oral malodor reducing agents; anti-attachment agents or sealants; diagnostic solutions; occluding agents; anti-inflammatory agents; dry mouth relief ingredients; catalysts to enhance the activity of any of these agents; colorants or aesthetic ingredients; and combinations thereof. The fluid in one embodiment is free of (i.e., is not) toothpaste. Instead, the active agent is intended to provide supplemental oral care benefits in addition to merely brushing one's teeth. Other suitable fluids could include lip balm or other materials that are typically available in a semi-solid state.

A dispensing orifice 318 is provided in the distal end 303 of the housing 301 through which fluid stored in the reservoir 317 can be dispensed from the dispenser 300. In the exemplified embodiment, the dispensing orifice 318 is located in a transverse end wall at the distal end 303 of the housing 301 and extends through the applicator 302. In certain other embodiments, the dispensing orifice 318 can be located in other areas of the housing 301, such as on one of the longitudinal side walls. In some embodiments, a plurality of dispensing orifices 318 can be provided. For example, the plurality of dispensing orifices 318 can be provided in a generally circular configuration that may be used to facilitate the fluid being dispensed through the applicator 302.

The applicator 302, in the exemplified embodiment, is formed of a soft resilient material, such as an elastomeric material. Suitable elastomeric materials include thermoplastic elastomers (TPE) or other similar materials used in oral care products. The elastomeric material of the outer layer may have a hardness durometer measurement ranging between A13 to A50 Shore hardness, although materials outside this range may be used. A suitable range of the hardness durometer rating is between A25 to A40 Shore hardness.

In alternative embodiments, the applicator 302 may be constructed of bristles, a porous or sponge material, or a fibrillated material. Suitable bristles include any common bristle material such as nylon or PBT. The sponge-like materials can be of any common foam material such as urethane foams. The fibrillated surfaces can be comprised of various thermoplastics. The invention, however, is not so limited and the applicator 302 can be any type of surface and/or configuration that can apply a viscous substance onto the hard surface of teeth, including merely an uncovered opening/orifice.

The exemplary applicator 302 comprises a tubular sidewall 359 and a transverse end wall 360. An aperture 361 (which can be considered a portion of the dispensing orifice 318) is provided in the end wall 360 through which fluid from the reservoir 317 can be dispensed. A plurality of protuberances 363, such as nubs, extends from the outer surface of the end wall 360.

The rotatable actuator 304 protrudes axially from the proximal end 305 of the housing 301 so that a user can easily grip and rotate the actuator 304. The actuator 304 comprises a dome portion 306 and an anti-rotation feature, which in the exemplified embodiment is in the form of two members 307A, 307B that extend axially from the dome portion 306 toward the distal end 303 of the housing 301 and overlie a portion of the outer surface 314 of the housing 301.

In the exemplified embodiment, the rotatable actuator 304 is rotatable with respect to the housing 301 and also axially reciprocates along axis B-B during rotation. The exemplified internal dispensing subsystem of the dispenser 300 generally comprises a reciprocator 308, an extension member 309, an elevator 310, and a collar 311. The reciprocator 308 comprises the rotatable actuator 304, a resilient member 312 and a drive screw 313. The rotatable actuator 304 is rotatably coupled to the housing 301. Upon rotation of the rotatable actuator 304 relative to the housing 301, the elevator 310 is translated axially along the drive screw 313, thereby forcing the fluid from the reservoir 317 through the dispensing orifice 318 and out of the applicator 302. While one embodiment of an internal dispensing subsystem is illustrated and described above, it is to be understood that a wide variety of mechanisms and subsystems can be used to dispense the fluid from the dispenser 300 in accordance with the present invention. The exact structural and functional details of the internal dispensing subsystem are not limiting of the present invention, unless specifically recited in a claim.

When the dispenser 300 is in the application state (as illustrated in FIGS. 3 and 5), the rotatable actuator 304 of the dispenser 300 can be rotated to dispense the fluid from the dispenser 300. More specifically, when the dispenser 300 is in the application state, the rotatable actuator 304 of the dispenser 300 can be rotated with respect to the housing 301 to dispense the fluid from the dispenser 300. As a result, the user can use the dispenser 300 to apply the fluid directly to the desired oral surface. However, when the dispenser 300 is in the storage state (as shown in FIGS. 1-2), it is desirable that the dispenser 300 be unable to dispense the fluid, which may occur due to inadvertent rotation of the rotatable actuator 304. Thus, the toothbrush 200 and the dispenser 300 are designed so that when the dispenser is in the storage state, the rotatable actuator 304 can not be rotated in a manner that would inadvertently dispense the fluid from the dispenser 300.

Figure 6:
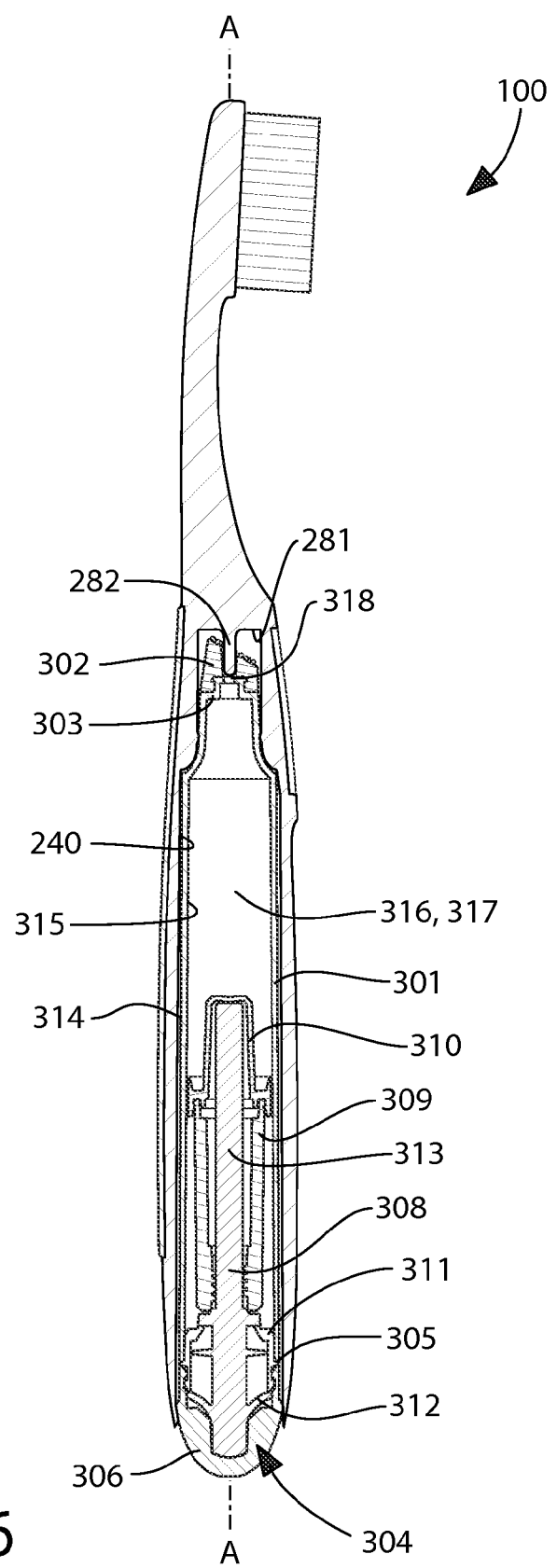
FIG. 6 is a longitudinal cross-sectional view of the oral care system of FIG. 1, wherein the fluid dispenser is in the storage state.

Referring now to FIGS. 1, 2 and 6 concurrently, the dispenser 300 is illustrated in the storage state. When in the storage state, the dispenser 300 is docked within the cavity 280 of the handle 210 of the toothbrush 200. An interference fit between the outer surface 314 of the dispenser 300 and an inner surface 240 of the toothbrush 200 detachably couples the dispenser 300 to the toothbrush 200. When the dispenser 300 is in the storage state, at least a portion, and preferably a majority, of the dispenser 300 is located within the internal cavity 280 of the toothbrush 200.

In the exemplified embodiment, the entirety of the housing 301 of the dispenser 300, including the applicator 302, are located within the cavity 280 of the toothbrush 200 when the dispenser 300 is in the storage state. Moreover, as can be seen in FIG. 6, the plug 282 of the toothbrush extends through a portion of the dispensing orifice 318 and seals the dispensing orifice 318 of the dispenser 300 when the dispenser 300 is in the storage state. In some embodiments, the extension of the plug 282 through a portion of the dispensing orifice 318 may assist with coupling the dispenser 300 within the cavity 280 of the toothbrush 200.

The rotatable actuator 304 of the dispenser 300 protrudes axially from the proximal end 212 of the handle 210 of the toothbrush 200 when in the storage state In this manner, the rotatable actuator 304 of the dispenser 300 forms a longitudinal extension of the handle 210 of the toothbrush 200. The dome portion 306 of the rotatable actuator 304 continues the natural contour of the handle 210 and provides a rounded proximal end to the oral care system 100, thereby providing a look that aesthetically resembles a traditional manual toothbrush.

While the housing 301 of the dispenser 300 is located within the cavity 280 of the toothbrush 200 and the rotatable actuator 304 protrudes from the handle 210 of the toothbrush 200, the rotatable actuator 304 can not be rotated relative to the toothbrush 200 (or relative to the housing 301 of the dispenser 300) due to a mechanical interference created between the anti-rotation feature of the rotatable actuator 304 and the anti-rotation feature of the toothbrush 200. In the exemplified embodiment, the anti-rotation feature of the rotatable actuator 304 comprises the two members 307A, 307B that extend from the dome portion 306 while the anti-rotation feature of the toothbrush 200 comprises two recesses 250A, 250B that are formed into a proximal edge 251 of the handle 210 of the toothbrush 200.

Figure 7:
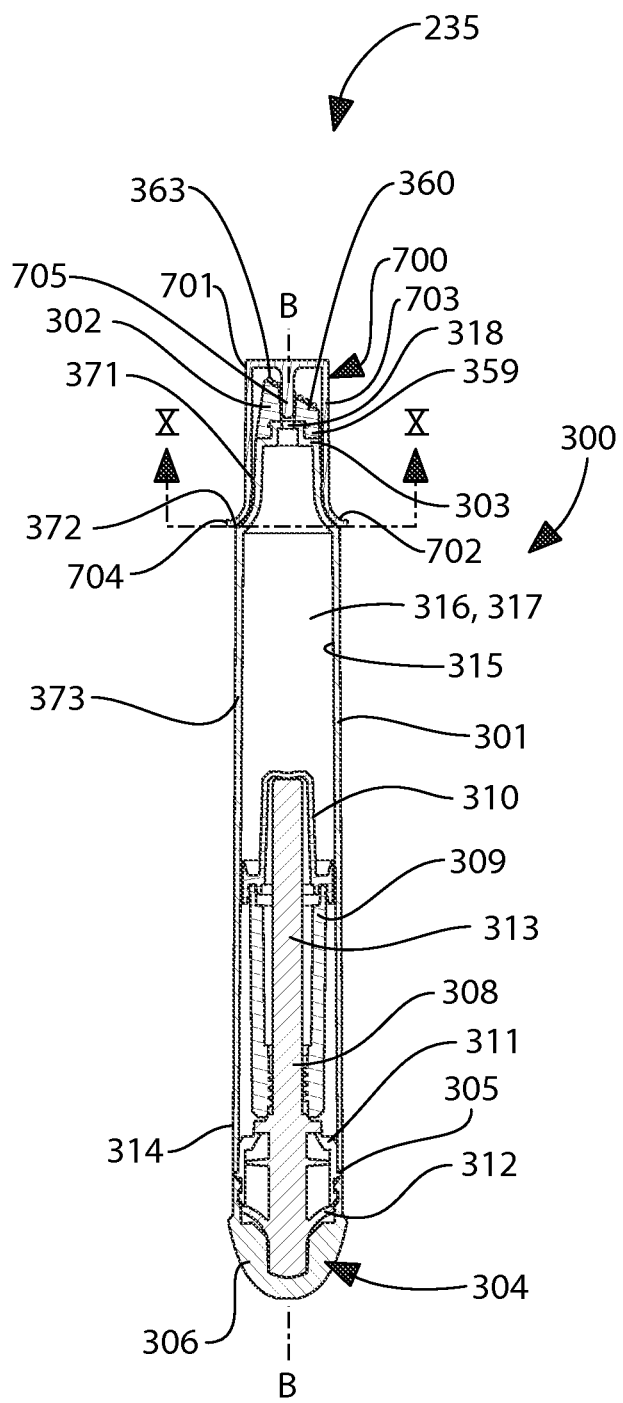
FIG. 7 is a transverse cross-sectional view of the fluid dispenser of FIG. 5 wherein a cap is detachably coupled to the dispenser.

Referring now to FIG. 7, the dispenser 300 is illustrated having a cap 700 detachably coupled thereto. The cap 700 comprises a closed top end and an open bottom end. The cap 700 also generally comprises a tubular portion 701 and a flanged portion 702 extending radially outward from a bottom end of the tubular portion 701. When the cap 700 is coupled to the dispenser 300, the nozzle portion 371 of the housing 301 is located within the tubular portion 701 of the cap 700 while the flanged portion 702 overlies and abuts the shoulder portion 732 of the housing 301 of the dispenser 300. The flanged portion 732 extends radially outward from the outer surface 703 of the tubular portion 701 and terminates at an annular flange edge 704. The cap 700 is designed so that when the cap 700 is coupled to the dispenser 300, the flanged portion 702 protrudes radially beyond the shoulder portion 732 of the housing 301.

While the flanged portion 702 of the cap 700 is exemplified as a continuous annular structure, the flange portion 702 could take on other forms. For example, in other embodiments, the flanged portion 702 may take the form of a segmented flange or radially extending struts.

Figure 10:
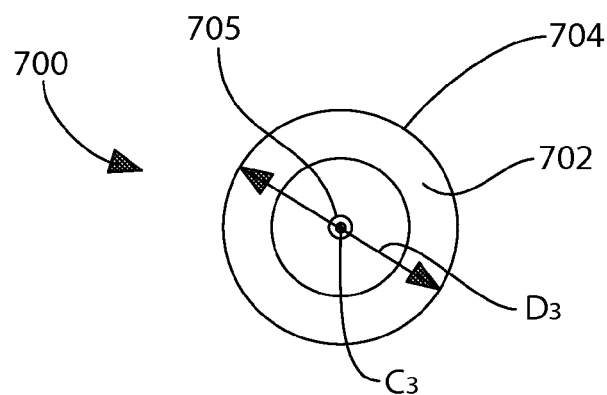
FIG. 10 is a transverse cross-sectional profile of the cap of FIG. 7 taken along view X-X of FIG. 7.

In the exemplified embodiment, both the tubular portion 301 and the flanged portion 702 of the cap have generally circular transverse-cross sectional profiles. However, the invention is not so limited and in other embodiments, the tubular portion 301 and/or the flanged portion 702 may have non-circular transverse cross-sectional profiles as desired. As can be seen in FIG. 10, the flanged portion 702 of the cap 700 has a center point $C_3$ and a diameter $D_3$ (measured to the flange edge 704). As discussed below, the size and/or shape of the transverse cross-sectional profile of the flanged portion 702 is selected to cooperate with the transverse cross-sectional profile of the opening 215 of the toothbrush 200 to prohibit the dispenser 300 from being fully inserted into the cavity 280 when the cap 700 is coupled to the dispenser 300.

In the exemplified embodiment, the cap 700 is coupled to the dispenser 300 via a mechanical interference fit. However, in other embodiments, the cap 700 can be detachably coupled to the dispenser 300 in other ways, such as by a threaded connection, a snap-fit connection, or the like. When the cap 700 is coupled to the dispenser, the cap 700 seals the dispensing orifice 318 so that the fluid within the reservoir 317 does not leak or dry out prior to its initial use. In order to seal the reservoir 317, the cap 700 is provided with a plug 705 that extends axially from a bottom surface of the closed top end of the cap 700. Thus, when the cap 700 is coupled to the dispenser 300, the plug 705 penetrates into and seals the dispensing orifice 318 of the dispenser 300.

Figure 11:
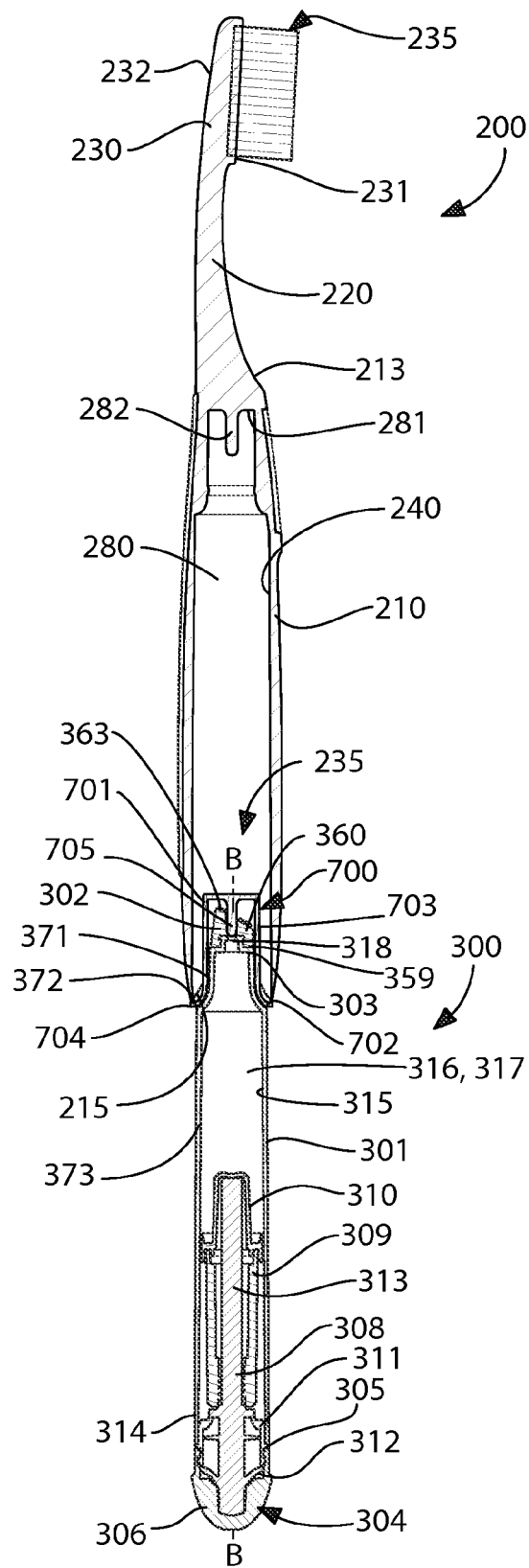
FIG. 11 is a longitudinal cross-sectional view of the fluid dispenser being prohibited from being inserted into the cavity of the toothbrush by nature of the cap being coupled to the dispenser.
Figure 12:
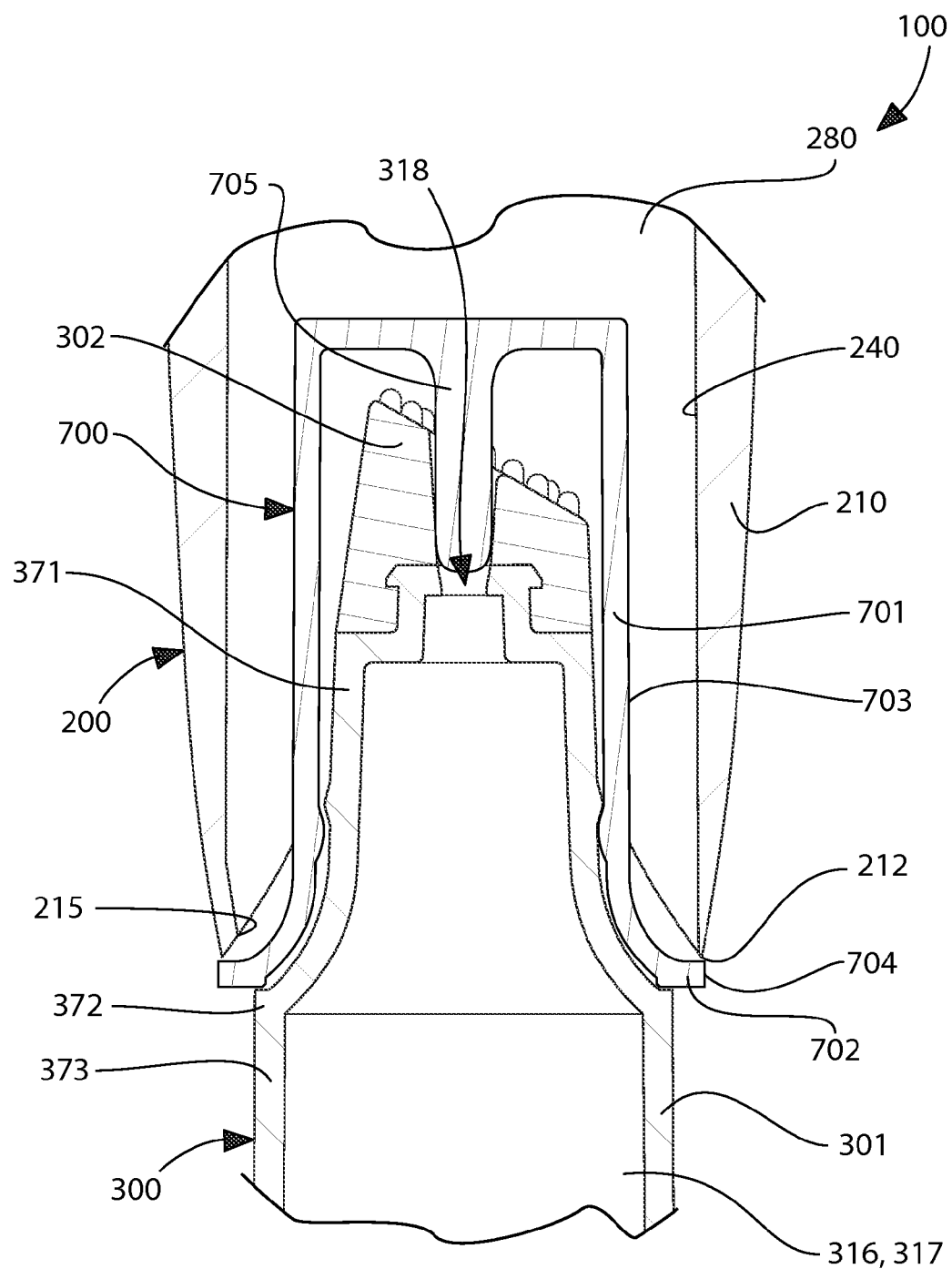
FIG. 12 is a close-up of area XII-XII of FIG. 11.

In certain embodiments of the present invention, it may be desirable to sell the oral care system 100 in an arrangement where the toothbrush 200 and the dispenser 300 are in an uncoupled state. In such a scenario, it will be desirable to couple the cap 700 to the dispenser 300 to preserve the fluid within the reservoir 317. However, once the oral care system 100 is to be used by a customer, the cap 700 is no longer necessary because the dispenser 300 will be docked in the cavity 280 of the toothbrush 200 where the plug 281 of the toothbrush 200 will seal the dispensing orifice 318 during periods of non-use. However, it is possible that the customer will attempt to insert the dispenser 300 with the cap 700 still attached thereto into the cavity 280 of the toothbrush 200. Such a situation is undesirable because the cap 700 could damage the plug 281 within the cavity 280 of the toothbrush or become lodged within the cavity, thereby preventing proper future functioning of the oral care system 100. Thus, in accordance with the present invention, the cap 700 is designed so that it can not pass through the opening 215 of the toothbrush 200. As a result, if the cap 700 is coupled to the dispenser 300, the dispenser 300 will be prohibited from being fully inserted into the cavity 280 and into the storage state because the cap 700 would be obstructed from passing through the opening 215 (see FIGS. 11-12). More specifically, the flange portion 702 of the cap 700 will contact portions of the proximal edge 251 of the toothbrush 200 and be unable to pass through the opening 215.

The aforementioned safety feature can be achieved by relatively designing the geometries of the cap 700, the opening 215 of the toothbrush 200, and the housing 301 of the dispenser 300 so that the cap 700 can not be translated through the opening 215 while the housing 301 of the dispenser 300 can be translated through the opening 215. For example, in some embodiments, the proximal edge 251 may include one or more recesses and the flange portion 702 may include one or more protuberances, such that the one or more protuberances may mate with the one or more recesses. In these embodiments, the recesses and the protuberances may help to prohibit the cap 700 from translating through opening 215.

Referring now to FIGS. 8-10 concurrently, the relative geometrical design of the cap 700, the opening 215 of the toothbrush 200, and the housing 301 of the dispenser 300 to achieve the aforementioned safety feature will be described in accordance with one embodiment of the present invention. Conceptually, in the exemplified embodiment of the oral care system 100, the aforementioned safety feature can be achieved by proper design of the transverse cross-sectional profiles of the opening 215 of the toothbrush 200, the flange portion 702 of the cap 700, and the shoulder portion 372 (and/or the barrel portion 373) of the housing 301 of the dispenser 300.

As mentioned above, the transverse cross-sectional profile of the opening 215 of the toothbrush 200 is circular in shape, having a diameter $D_1$ and a center point $C_1$. The transverse cross-sectional profile of the flange portion 702 of the cap 700 is also circular but instead has a diameter $D_2$ and a center point $C_2$. The diameter $D_2$ is greater than the diameter $D_1$. Thus, when the center points $C_1$, $C_2$ of the transverse cross-sectional profiles of the flange portion 702 and the opening 215 are aligned, the transverse cross-sectional profile of the flange portion 702 does not fit entirely within the transverse cross-sectional profile of the opening 215. As a result, the flange portion 702 of the cap 700 can not pass through the opening 215 of the toothbrush 200. Therefore, if the cap 700 remains coupled to the dispenser 300, the dispenser 300 will be prohibited from being fully inserted into the cavity 280 of the handle 210 and into the storage state (shown in FIG. 11-12).

Regarding the dispenser 300, the transverse cross-sectional profile of the shoulder portion 372 (and the barrel portion 373) is also circular and has a diameter $D_3$ and a center point $C_3$. The diameter $D_3$ is less than the diameter $D_1$. Thus, when the center points $C_1$, $C_3$ of the transverse cross-sectional profiles of the opening 215 and the shoulder portion 372 (or barrel portion 373) are aligned, the transverse cross-sectional profile of shoulder portion 372 (or barrel portion 373) of the housing 301 fits entirely within the transverse cross-sectional profile of the opening 215. As a result, the housing 301 of the dispenser 300 can pass through the opening 215 of the toothbrush 200 and into the cavity 280 until the dispenser 300 is in the storage state (as shown in FIG. 6).

The aforementioned geometric principles can be applied to any shape (or shapes) that the transverse cross-sectional profiles of the opening 215, the cap 700, and the housing 301 may take on, whether or not the shapes are similar or dissimilar, and/or circular or non-circular. For example, assume that the opening 215 has a transverse cross-sectional profile that is circular in shape and has a diameter $D_1$ and a center point $C_1$. Now assume that the flange portion 704 (or another portion) of the cap 700 has transverse cross-sectional profile that is rectangular shape having a diagonal and a center point. In this scenario, the flange portion 602 of the cap 700 should be designed so that the diagonal of its rectangular transverse cross-sectional profile is greater than the diameter $D_1$ of the transverse cross-sectional profile of the opening 215. When the diagonal is greater than the diameter $D_1$, the rectangular transverse cross-sectional profile of the flange portion 702 of the cap 700 will not fit entirely within the circular transverse cross-sectional profile of the opening 215 (the corners of the rectangle will lie outside of the perimeter of the circle). As a result, the cap 700 will prohibit the dispenser 300 from being fully inserted into the cavity 280 of the toothbrush 200 while the cap 700 is coupled thereto. Of course, similar calculations can performed for any and all geometries.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

While the foregoing description and drawings represent the exemplary embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, sizes, and with other elements, materials, and components, without departing from the spirit or essential characteristics thereof. One skilled in the art will appreciate that the invention may be used with many modifications of structure, arrangement, proportions, sizes, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being defined by the appended claims, and not limited to the foregoing description or embodiments.

What is claimed is:

1. An oral care system comprising:
   a toothbrush having a cavity and a plug in the cavity, an opening forming a passageway into the cavity;
   a dispenser comprising a housing having a reservoir containing a fluid and a dispensing orifice;
   a cap detachably coupled to the dispenser that seals the dispensing orifice, the cap comprising a tubular portion and a flange portion;
   wherein the flange portion of the cap has a diameter that is greater than a maximum diameter of the housing of the dispenser, and wherein the flange portion of the cap can not fit through the opening so that when the cap is coupled to the dispenser, the cap prohibits the dispenser from being inserted into the cavity; and
   wherein when the cap is detached from the dispenser, the dispenser can be fully inserted into the cavity so that the plug penetrates the dispensing orifice and the dispenser is detachably coupled to the toothbrush.

2. The oral care system according to claim 1 wherein the cavity is located in a handle of the toothbrush and extends along a longitudinal axis of the handle.

3. The oral care system according to claim 2 wherein the opening is located at a proximal end of the handle, and wherein the flange portion of the cap has a transverse cross-section profile that can not fit through a transverse cross-sectional profile of the opening.

4. The oral care system according to claim 1 wherein the housing comprises a nozzle portion and a shoulder portion, the nozzle portion located within the tubular portion of the cap and the flange portion of the cap protruding radially beyond the shoulder portion of the dispenser when the cap is coupled to the dispenser.

5. The oral care system according to claim 1 wherein the dispenser comprises a shoulder portion, the flange portion of the cap protruding radially beyond the shoulder portion of the dispenser when the cap is coupled to the dispenser.

6. The oral care system according to claim 1 further comprising an applicator located at a distal end of the housing and fluidly coupled to the dispensing orifice, and an actuator for dispensing the liquid from the reservoir to the applicator.

7. The oral care system according to claim 1 wherein the opening has a first transverse cross-sectional profile, the flange portion of the cap having a second transverse cross-sectional profile that does not fit entirely within the first transverse cross-sectional profile, and the housing of the dispenser having a third transverse cross-sectional profile that fits entirely within the first transverse cross-sectional profile.

8. The oral care system according to claim 1 wherein the plug extends axially from a transverse end wall of the cavity.

9. An oral care system comprising:
   a toothbrush having a cavity extending along a longitudinal axis and an opening forming a passageway into the cavity, the opening having a first transverse cross-sectional profile;
   a dispenser comprising a housing having a reservoir containing a fluid and a dispensing orifice, the housing having a second transverse cross-sectional profile that fits entirely within the first transverse cross-sectional profile; and a cap detachably coupled to the dispenser, the cap having a portion having a third cross-sectional profile that does not fit entirely within the first transverse cross-sectional profile.

10. The oral care system according to claim 9 wherein the portion of the cap is a flange portion.

11. The oral care system according to claim 9 wherein when the cap is coupled to the dispenser, the portion of the cap prohibits the dispenser from being inserted into the cavity.

12. The oral care system according to claim 9 wherein when the cap is detached from the dispenser, the dispenser can be inserted into the cavity and detachably coupled to the toothbrush.

13. The oral care system according to claim 9 wherein the first transverse cross-sectional profile comprises a center point, the second transverse cross-sectional profile comprises a center point, and the third transverse cross-sectional profile comprises a center point, and wherein when the center points of the first, second and third transverse cross-sectional profiles are concentric, the third cross-sectional profile does not fit entirely within the first transverse cross-sectional profile and the second transverse cross-sectional profile fits entirely within the first transverse cross-sectional profile.

14. The oral care system according to claim 9 wherein the second transverse cross-sectional profile of the housing of the dispenser is taken at a shoulder portion of the housing.

15. The oral care system according to claim 9 wherein the toothbrush further comprises a plug extending axially from a transverse end wall of the cavity, wherein when the cap is detached from the dispenser, the dispenser can be inserted into the cavity so that the plug penetrates and seals the dispensing orifice and the dispenser is detachably coupled to the toothbrush.

16. The oral care system according to claim 9 wherein the cap further comprises a plug that penetrates and seals the dispensing orifice when the cap is coupled to the dispenser.

17. An oral care system comprising:
a toothbrush having a cavity;
a dispenser comprising a reservoir containing a fluid;
a cap detachably coupled to the dispenser;
wherein the cap comprises a portion that can not be translated through an opening that forms a passageway into the cavity so that when the cap is coupled to the dispenser, the cap prohibits the dispenser from being inserted into the cavity; and
wherein when the cap is detached from the dispenser, the dispenser can be inserted into the cavity and detachably coupled to the toothbrush.

18. The oral care system according to claim 17 wherein the portion of the cap comprises a flange portion that protrudes radially beyond a shoulder portion of a housing of the dispenser when the cap is coupled to the dispenser.

19. The oral care system according to claim 17 wherein the toothbrush further comprises a plug extending axially from a transverse end wall of the cavity, wherein when the cap is detached from the dispenser, the dispenser can be inserted into the cavity so that the plug penetrates and seals a dispensing orifice of the dispenser and the dispenser is detachably coupled to the toothbrush.

20. The oral care system according to claim 19 wherein the cap further comprises a plug that penetrates and seals the dispensing orifice of the dispenser when the cap is coupled to the dispenser.

* * * * *